United States Patent
Rigby et al.

(10) Patent No.: US 8,012,516 B2
(45) Date of Patent: *Sep. 6, 2011

(54) FEEDS CONTAINING HOP ACIDS AND USES THEREOF AS SUPPLEMENTS IN ANIMAL FEEDS

(76) Inventors: Francis L. Rigby, Yakima, WA (US); John Segal, Larchmont, NY (US); Janet Z. Segal, legal representative, Larchmont, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/479,429

(22) Filed: Jun. 5, 2009

(65) Prior Publication Data

US 2009/0297646 A1 Dec. 3, 2009

Related U.S. Application Data

(63) Continuation of application No. 11/060,382, filed on Feb. 17, 2005, now Pat. No. 7,553,504.

(60) Provisional application No. 60/546,167, filed on Feb. 23, 2004.

(51) Int. Cl.
*A61K 36/66* (2006.01)
*A61K 36/00* (2006.01)

(52) U.S. Cl. ........................................ 424/750; 424/725

(58) Field of Classification Search ................. None
See application file for complete search history.

(56) References Cited

U.S. PATENT DOCUMENTS

| | | | |
|---|---|---|---|
| 2,592,348 A | 4/1952 | Siefker et al. | |
| 4,170,638 A | 10/1979 | Owades | |
| 4,344,978 A | 8/1982 | Sharpe et al. | |
| 5,082,975 A | 1/1992 | Todd, Jr. et al. | |
| 5,114,708 A | 5/1992 | Hunter et al. | |
| 5,286,506 A | 2/1994 | Millis et al. | |
| 5,370,863 A | 12/1994 | Barney et al. | |
| 5,455,038 A | 10/1995 | Barney et al. | |
| 5,641,517 A | 6/1997 | Eskeland et al. | |
| 5,702,737 A * | 12/1997 | Guzinski et al. | 426/33 |
| 5,783,235 A | 7/1998 | Ting et al. | |
| 5,917,093 A * | 6/1999 | Ting et al. | 568/366 |
| 6,129,907 A | 10/2000 | Sreenivasan et al. | |
| 6,251,461 B1 | 6/2001 | Johnson et al. | |
| 6,379,720 B1 | 5/2002 | Newmark et al. | |
| 6,391,346 B1 | 5/2002 | Newmark et al. | |
| 6,423,317 B1 | 7/2002 | Haas et al. | |
| 6,451,365 B1 | 9/2002 | King et al. | |
| 6,475,537 B1 | 11/2002 | King et al. | |
| 6,849,287 B1 | 2/2005 | Rader et al. | |
| 7,090,873 B2 | 8/2006 | Maye | |
| 2001/0031305 A1 | 10/2001 | Smith et al. | |
| 2002/0110619 A1 | 8/2002 | Rader et al. | |
| 2002/0197366 A1 | 12/2002 | King et al. | |
| 2003/0008021 A1 | 1/2003 | Babish et al. | |
| 2003/0013773 A1 | 1/2003 | Haas et al. | |
| 2003/0015480 A1 | 1/2003 | Breen et al. | |
| 2003/0228814 A1 | 12/2003 | Barney et al. | |
| 2004/0002423 A1 | 1/2004 | Ohnogi et al. | |
| 2004/0018284 A1 | 1/2004 | Kuethe et al. | |
| 2004/0044087 A1 | 3/2004 | Maye et al. | |
| 2004/0137097 A1 | 7/2004 | Maye | |

FOREIGN PATENT DOCUMENTS

| | | |
|---|---|---|
| EP | 0 606 599 A1 | 7/1994 |
| EP | 0 681 029 | 7/1997 |
| EP | 1 277 473 A1 | 1/2003 |
| GB | 2848 AD | 10/1913 |
| GB | 120166 A | 10/1918 |
| GB | 132 597 | 9/1919 |
| GB | 2 072 657 A | 1/1981 |
| GB | 2 330 076 | 4/1999 |
| JP | 01-172340 A | 7/1989 |
| JP | 01172341 A | 7/1989 |
| RU | 2075298 C1 | 3/1997 |
| WO | WO 01/76614 A1 | 10/2001 |
| WO | WO 03/097079 | 11/2003 |
| WO | WO 2004/026041 A1 | 4/2004 |

OTHER PUBLICATIONS

XP-002268355 (Database WPI) Derwent Publications Ltd.
V.E. Buckwold et at., Antiviral Constituents of Hops Against a Series of DNA and RNA Viruses, J. Antiviral Research, 61:57-62, 2004.
G. Gerthauser at al., Cancer Chemopreventative Activity of Xanthohumol, A Natural Product Derived from Hop, Molecular Cancer Therapeutics, 1:959-969, Sep. 2002.
J.C. Lewis et al., Lupulon and Humulon—Antibiotic Substituents of Hops, J. Clinical Investigations, vol. XXVII, p. 916-919, Sep. 1949.
C.L. Miranda et al., Antiproliferative and Cytotoxic Effects of Prenylated Flavanoids from Hops (*Humulus lupulus*) in Human Cancer Cell Lines, Food and Chemical Technology, 37:271-285, 1999.
C.L. Miranda et al., Antioxidant and Prooxidant Actions of Prenylated and Non-Prenylated Chalcones and Flavones In Vitro, J. Ag. and Food Chem., 48:3876-3884, 2000.

(Continued)

*Primary Examiner* — Christopher R Tate
*Assistant Examiner* — Deborah A. Davis
(74) *Attorney, Agent, or Firm* — Kenyon & Kenyon LLP

(57) ABSTRACT

Disclosed are methods for administering hop acids to alter the microbial population of the gastrointestinal tract of animals and to inhibit the growth of pathogenic organisms in the gastrointestinal tracts of animals. Also disclosed are methods of increasing weight gain, feed efficiency, milk production in mammals, and egg and meat production in poultry by administering hop acids. Also disclosed are animal feeds containing hops and hop acids.

17 Claims, No Drawings

OTHER PUBLICATIONS

A.F. Schmalreck et al., Structural Features Determining the Antibiotic Potencies of Natural and Synthetic Hop Bitter Resins, Their Precursors and Derivatives, Can. J. Microbiology, 31:205-212, 1974.

M. Shigeyuki and Y. Sato, A New Flavone with Antifungal Activity Isolated from Hops, Agric. Biol. Chem. 48:2771-2775, 1984.

J.F. Stevens, Chemistry and Biology of Hop Flavanoids, J. Am. Soc. Brew. Chem. 56:136-145, 1988.

Declaration of Francis Lloyd Rigby, Jul. 11, 2006.

Starvi, Michael et al., "The Antimycobacterial Components of Hops (*Humulus lupulus*) and their Dereplication," *Phytotherapy Research* vol. 18, No. 9, 2004, pp. 774-776.

Beuchat et al. "Antimicrobials Occurring Naturally in Foods." *Food Technology. Institute of Food Technologists.* Chicago, US. vol. 43, No. 1, 1989, 134-142.

FASS, 1999. *Guide for the Care and Use of Agricultural Animals in Agricultural Research and Teaching. 1st rev. ed.* Federation of Animal Science Societies. Savoy IL.

Starvi, M., R. Schneider, G. O'Donnell, D. Lechner, F. Bucar, and S. Gibbons, 2004. "The antimycobacterial components of hops (*Humulus lupulus*) and their dereplication." *Phytotheraov Research*. 18:774-776.

Stevens, J.F., and J. E. Page, 2004. "Xanthohumol and related prenylflavonoids from hops and beer: to your good health!" *Phytochemistry*. 65:1317-1330.

Walker, C., 2003. "Hops and Health." *Hmeljarski-Bilten*. 10:5-11.

Arnould, R., J., M. Bouquiaux, and M. Vanbelle, "*Using Brewer's Waste (Malt and Hops) for Feeding Dairy Cows*," Revue de l'Agric., 36 (1983), pp. 93-105 (with abstract).

Cvak Z., J. Kvasnicaic, J. Rejijolec, and K. Zadrazil, "*The Effect of Feeding Hops on Quality and Public Health Parameters of Cow Milk," Veterinarstvi.*, 37 (1987), pp. 79-81 (with abstract and English translation).

Daenicke, R., K. Rohr, and F.P. Engling, "*Influence of Brewer's Spent Hops Silage in diets for Dairy Cows on Digestion and Performance Variables" Umweitaspekte der Tierproduktion.*, 33 (1991), pp. 539-544 (with abstract).

M.E. Ensminger, Ph.D.; J.E. Oldfield, Ph.D.; W.W. Heinemann, Ph.D., *Feeds & Nutrition Digest*, second edition, *The Ensmincier Publishing Company*, California, (1990) pp. 118-119.

*The Stockman's Handbook (Animal Agriculture Series)*, seventh edition, *Interstate Publishers, Inc*., Illinois, p. 486.

G. Krishna at at., Fermentation of Various Preparations of Spent Hops (*Humulus lupulus* L.) Using the Rumen Simulation Technique (Rusitec), Agricultural Wastes, 17 (1986) pp. 99-117.

Larson et al.: "Antimicrobial activity of hop extracts against *Listeria monocytogenes* in media and in food", International Journal of Food Microbiology, vol. 33, 1996; pp. 195-207.

Haunold, Alfred, et al., "Development of Zero-Alpha Hop Genotypes," *Crop Science*, vol. 17, Mar.-Apr. 1977, pp. 315-319.

Batchvarov, V and G. Marinova, 2001. "Healthy ingredients in malt, hops, and beer." *Khranitelnovkusova-Promishlenost*. 50:15-17.

Batchvarov, Valentin, et al., Micro-Ingredients with Health-Beneficial Effects in Malt, Hops and Beer, vol. 50, No. 9, 2007, pp. 12-14.

G. Pollach, W. Hein, and F. Hollaus, "*Use of Hop Products as Bactereostatic Agents in the Sugar Industry*," ZuckerIndustrie, 121. 919-926 (1996).

* cited by examiner

FEEDS CONTAINING HOP ACIDS AND USES THEREOF AS SUPPLEMENTS IN ANIMAL FEEDS

CROSS REFERENCE TO RELATED APPLICATIONS

This application is a continuation of application Ser. No. 11/060,382 filed on Feb. 17, 2005 now U.S. Pat. No. 7,553,504, and claims the benefit of provisional patent application No. 60/546,167, filed on Feb. 23, 2004, which is incorporated herein in its entirety by reference.

BACKGROUND OF THE INVENTION

Several approaches have been taken toward enhancing growth and feed utilization in food animals. These approaches, which include the use of antibiotics and biological compounds such as growth hormones and growth hormone releasing factors, have either unacceptable side effects, public health consequences, a social stigma, or they are too expensive for producers to implement profitably. Antibiotic supplementation has been used to treat diseases, enhance feed utilization, and to otherwise benefit the health and/or metabolism of food producing animals. The use of antibiotics allows greater production from animals (e.g., in the form of meat, eggs and milk) from the same quantity of feed, thus allowing greater potential for profitability. However, as awareness has increased to the potential danger of resistance to antibiotics used in the treatment of people, there has been growing pressure from consumers and governmental authorities to avoid using such antibiotics as feed additives in animals. Indeed, as a result of increasing consumer pressure and in particular concerns about increased microbial resistance to antibiotics, a ban on the use of antibiotic growth promoters in animal feed has already been introduced in Germany. In 1998, the European Union banned antibiotics important in human medicine from use as growth promoters in livestock production.

There is considerable evidence that the development of resistant organisms is reducing the number of effective antibiotics available for doctors to treat bacterial infections successfully. The more microorganisms that become resistant to antibiotics, the greater the risk of a resurgence of untreatable infectious diseases. The overuse of antibiotics in livestock feed is believed to be a major factor contributing to the increase in antibiotic resistance. A majority of the antibiotics used in animal husbandry today are not used to treat sick animals, but rather to promote more efficient growth and utilization of feed.

Used properly, subtherapeutic administration of antimicrobials and antibiotics as feed supplements in farm animals increases production of meat and milk per pound of food fed and enables producers to provide consumers with a lower-cost product. By reducing the risk of outbreak of some diseases, and enhancing growth rates and feed efficiency, the use of these agents allows animals to grow bigger faster. The effect on growth may be due to suppression of harmful bacteria in the digestive tract, which helps maintain the proper absorption of nutrients. The administration of subtherapeutic levels of antibiotics also may exert a modulating effect on the metabolic activity of certain intestinal bacteria or it may shift the balance of the microbial ecosystem, which constitutes an essential part of digestion. The positive effects may also be due to the antibiotics killing or inhibiting the growth of organisms that would otherwise make the animals ill. Animals that are ill generally do not eat properly and their growth rate and overall health therefore diminish.

Thus, there is a need for methods of enhancing the growth and feed efficiency of animals by administering or feeding antibiotics that are not traditionally used in medicine to treat bacterial infections, thus decreasing the danger of increasing resistance to those traditional antibiotics. There is also a need for animal feedstuffs containing antibiotics that will enhance the physical performance of animals while not adding to the problem of increasing bacterial resistance to medically useful antibiotics. The present invention meets these needs.

SUMMARY OF THE INVENTION

The present invention provides methods of altering the microbial population of the gastrointestinal tract of an animal. These methods comprise administering to the animal a palatable amount of hop acids. The hop acids are administered orally, preferably in either the animal's feed or water.

The present invention also provides methods for inhibiting and/or modulating the growth of micro-organisms in digestive tracts of animals. These methods comprise administering hop acids or hops containing hop acids to the animals, whereby the animal ingests the hop acids or hops, and the hop acids present in the digestive tract of the animal reduce or inhibit growth of the micro-organisms in the digestive tract of the animal.

Another embodiment of the present invention provides methods for increasing feed efficiency in animals. These methods comprise feeding hop cones or hop acids to the animals. The presence of hop acids in the animals' digestive tract provides for an increase in feed efficiency over feed efficiency in animals not ingesting the hop cones or hop acids.

In other embodiments, the present invention provides methods for increasing weight gain in animals. These methods comprise feeding hop cones or hop acids to the animals, wherein the presence of the hop acids in the animal's digestive tract provides an increase in weight gain over the weight gain observed in animals not ingesting the hop cones or hop acids.

The present invention also provides methods of increasing milk production in dairy animals. These methods comprise feeding hop cones or hop acids to the dairy animals. The presence of hop acids in the dairy animals' digestive tracts provides an increase in milk production over the milk production in dairy animals not ingesting the hop cones or hop acids.

The present invention also provides methods of increasing egg production in poultry. These methods comprise feeding hop cones or hop acids to the poultry. The presence of hop acids in the birds' digestive tracts provides an increase in egg production over the egg production in poultry not ingesting the hop cones or hop acids.

In each of the methods above, the hop acids may comprise alpha acids with substantially no beta acids or beta acids with substantially no alpha acids. The hop acids may also comprise mixtures of hop acids. The hop acids may include iso-forms of the hop acids or salts of the hop acids. The hop acids may be administered in the form of milled hop plants (in particular the cones) that are mixed into the animals' feed. Any of several varieties of hop plants may be used. In a preferred embodiment, the hop plant is a variety having a higher beta acid content than alpha acid content, such as TEAMAKER.

The hop acids utilized according to the invention may also be chemically synthesized or extracted from the hops plants and administered orally in any number of methods known to those skilled in the art. For example, the hop acids may be administered as part of a lick, or in cubes, or in oral boluses mixed into flavoring substances or liquid feed (such as molasses), or as solutions of hop acids that are sprayed onto or mixed into the animals' feed or mixed into the animals' water. The hop acids may be extracted from the hop cones or chemically synthesized. The hop acids may be in their naturally occurring form or they may be chemically modified according to methods known in the art. Such chemical modifications may, for example, influence the solubility, efficacy, potency, stability, or taste of the hop acids.

The hop acids are administered in an effective amount with the dosage generally being expressed as the amount of hops acids per pound of animal being supplemented. Alternatively, when hop cones are milled and added to animal feed, the amount to be administered may be expressed as the weight of dried hops per pound of animal feed. Likewise, the concentration of the supplement may be expressed as the amount of hop acids per pound of animal feed. Different animals, such as cattle, swine or poultry, will require administration of the hop acids at different rates. The hop acids are administered in an effective amount according to the weight of the animal ingesting the hop acids. The hop additive may be used in the feed or water at concentrations below that at which the feed becomes bitter to the animal and unpalatable.

Animals that could benefit from supplementation in accordance with the invention include any warm or cold blooded animals, including but not limited to mammals (e.g., cattle, sheep, goats, swine, horses, etc.), poultry (e.g., chickens, turkeys, quail, ducks, geese, etc.), fish and crustaceans (e.g., salmon, catfish, tilapia, trout, shrimp, etc.), and pets of all kinds (e.g., dogs, cats, ferrets, and other pocket pets such as rodents and the like).

In other embodiments, the present invention provides animal feeds comprising milled hops or hop acids and isomers and modifications of hop acids, as well as pharmaceutically acceptable salts thereof.

DETAILED DESCRIPTION

The present invention provides methods for altering the microbial population and/or metabolic activity of microbes inhabiting the gastrointestinal tracts of animals. In particular embodiments, the invention provides methods for inhibiting the growth or altering the metabolic activity of pathogenic organisms in the gastrointestinal tracts of animals. The methods comprise administering hops or hop acids to animals, either in their feed or water.

The hop plant (*Humulus lupulus*) has been used in the brewing of beer since the middle ages when it was discovered that when hops were used in the brewing process, the beer rarely went sour during fermentation. This finding was so important that hops became widely used for this purpose and the bitter taste accompanying their use became the accepted flavor of malt beverages.

It is now known that the agents in hops responsible for the preservative value are two groups of complex enolic acids, called alpha and beta acids. These acids are found in glands called "lupulin" in the "cones" of the hops plant. The term "cone" is used here to refer to the structure that is also referred to variously in the art as the raceme, catkin, strobilus, strobile, or ament. The acids found in hop cones are naturally-occurring antibiotics that are not currently in regular medical use to treat infections. The alpha acids consist of three very similar major acids, called humulone, cohumulone and adhumulone. The beta acids consist of lupulone, colupulone and adlupulone. The alpha acids are transformed to isomers during the boiling of the brewer's wort in the brew kettle; these isomers are named isohumulone, isocohumulone, and isoadhumulone, respectively, and they are the compounds that impart the hop flavor to beer. The beta acids and any unisomerised alpha acids are largely lost from the brew during the making of beer because, owing to their low solubility, they are adsorbed on the yeast and precipitated proteins and carried off in the foam formed in the fermenter. The beta acids contribute to beer bitterness by being transformed to substances called hulupones, which usually impart about five percent of the total bitter flavor of beer. Only trace amounts of unisomerised alpha acids occur in beer.

Scientists have also learned that potency, stability, solubility, and other characteristics of the hop acids can be modified by hydrogenating the acids with, for example, the addition of two, four, or six hydrogen atoms, giving rise to di-, tetra-, and hexa-forms of the original acids or iso-acids. Both cis and trans forms of the iso-alpha acids also exist.

Hop acids have antibiotic activity against bacteria. For example, U.S. Pat. No. 6,451,365 claims a method for reducing gram-positive bacteria in food products by treating the surfaces of the food product with a composition comprising a gram-positive bacteriostatic compound and hop beta acids or hop beta acid derivatives. As another example, U.S. Pat. No. 6,475,537 claims applying a composition including hop acids and a chelating agent to a food surface or a non-food product to reduce or eliminate gram-positive spoilage or pathogenic bacteria, especially strains of *Listeria monocytogenes*. It is also known that hydrogenated beta acids may be added to antibacterial oral compositions such as toothpaste or mouthwash to inhibit bacterial growth. See U.S. Pat. No. 6,129,907. U.S. Patent Application No. 2003/0013773 discloses a method of sanitizing udders and teats of dairy cows by applying an aqueous solution of hop extracts. Hop extracts are also effective against protozoa. See e.g., U.S. Pat. No. 6,423,317.

While not being bound by any particular theory, mechanisms by which subtherapeutically administered amounts of antibiotics exert their effect on metabolism have been understood for many years and are concisely described by Dyer. (Betsy Dexter Dyer, A Field Guide to Bacteria, Cornell University Press 2003). All animals have an intestinal digestive chamber of some kind. In cattle, for example, it is the rumen, an organ in which microorganisms break down the feed into utilizable nutrients. Ruminants evolved as grazers, depending primarily on grass for growth and energy, and the microflora of the rumen are adapted to digest such cellulosic feeds. The feeds administered today under non-range conditions are high energy nutrient rich mixtures of grains and high protein fodder, supplemented with vitamins and minerals. These feeds are designed to produce more meat, milk and/or wool more quickly and more economically. The microflora of the rumen has changed to adapt to this rich diet, with the proliferation of different kinds of organisms. Foremost among these are strains of *Lactobacillus* and other organisms that produce lactic acid. This increase in acidity places the animal under stress and feed utilization diminishes. The hop acids are very effective antibiotics for the control of these organisms. The concentration in the brewing process, where the hop acids suppress the growth of lactobacilli, is commonly about 10 to 14 ppm, but ranges from about 5 to about 40 ppm. The hop acids are not used clinically because they are only slightly soluble in blood and would precipitate immediately if injected into body tissue, but they can function in the intestinal tract of an animal just as they do in a brewery fermenter. It is unlikely that they would pass through the intestinal wall because of their low solubility, but they would be harmless in any case as evidenced by their having been consumed in the human diet for centuries. It is significant also that pathogens enter the bodies of most animals through ingested food; it is, therefore, logical to combat these in the digestive tract before they proliferate and pass their toxins into the blood stream.

When an animal ingests hop acids, the acids will, because of their antibacterial properties, alter the microbial population in the gastrointestinal tract by killing or reducing or inhibiting the growth of micro-organisms, including pathogenic micro-organisms, thereby enhancing feed utilization and efficiency. However, in terms of their oral administration, the hop acids, especially the alpha acids, impart a bitter flavor that can cause animals to decrease their food intake. Thus, if the acids are added to an animal feed at excessive concentrations, they can actually decrease an animal's rate of growth by decreasing food intake. However, the hop acids exert their antibiotic effects at concentrations below those at which they impart a substantial enough bitter flavor to significantly decrease palatability. When the acids are administered at concentrations below those at which they begin to significantly effect palatability, they provide their growth-enhancing benefits without decreasing food consumption because of their bitter flavor. Thus, in one aspect, the present invention provides methods of enhancing the growth rate and feed utilization of animals by administering hop acids to animals at palatable concentrations. The inventors performed taste tests using prepared mixtures of hops in milled oatmeal at concentrations of hop acids corresponding to a daily intake by an animal of about 100 mg to 200 mg. The taste imparted by the acids at these levels was barely detectable and not unpleasant, and as such, these concentrations (and even higher concentrations) could be considered palatable.

Hops can be fed to animals by mixing it in with animal feed. The cones of the hop plant contain yellow glands, which contain resins containing the hop acids. Thus, the cones of the hop plant can be kiln dried, then milled, and mixed in with animal feed. Alternatively, the lupulin glands can be separated out of the cones by a physical process, yielding a free-flowing powder called "lupulin." This product comprises about 20 percent of the weight and 5 percent of the volume of the original hop cones, but contains all of the hop acids present in the cones prior to processing. This separation process is described in EP 1100865 and related co-pending U.S. application Ser. No. 09/126,495, filed Jul. 29, 1998, which are incorporated herein by reference in their entireties. The lupulin can be readily mixed into animal feed. The hop acids may also be extracted from the hop cones, by methods known in the art, such as but not limited to, extraction with carbon dioxide under sub-critical or super-critical conditions, or extracted with organic solvents. See U.S. Pat. Nos. 4,554,170 and 4,640,841, which are incorporated herein by reference in their entirety.

In addition, methods are known in the art for separating the alpha and beta acids from one another. The alpha and beta acids can be separated from a complete hop extract by phase separation procedures because of the difference in their pKa values. The alpha acids form salts with alkalis at a lower pH than do beta acids. As an example, a carbon dioxide extract of hop cones is made freely fluid by warming to about 130° F. and an aqueous solution of potassium hydroxide is slowly added, with vigorous stirring, until the aqueous phase is about pH 8.5. At this pH the alpha acids are present in the aqueous phase as the potassium salts. The beta acids remain in the resin phase together with some other insoluble components. The aqueous phase containing the alpha acids is separated and can be used as the basis for further reaction in which the alpha acids are isomerised to isoalpha acids. The remaining resin phase is then again contacted with additional potassium hydroxide, with vigorous stirring, and the potassium hydroxide is added until the aqueous phase is about pH 13. At this point the beta acids are in the aqueous phase as potassium salts and can be separated in the aqueous phase. This process is well known in the art, and it provides a method for separating solutions of alpha acids, isoalpha acids and beta acids, which may then be used in the animal feeds according to the invention. The invention includes the use of the hop acids and modifications of the acids outlined here, and in addition includes the use of any pharmaceutically acceptable salts of those acids (e.g., potassium and sodium salts). Hop acids are also commercially available from KALSEC Inc., P.O. Box 50511, Kalamazoo, Mich., 49005; S. S. Steiner, Inc. 655 Madison Ave., New York, N.Y., 10021; and John I. Haas, Inc., 5185 MacArthur Blvd, NW Washington, D.C. 20016. In addition, hop acids can be synthesized by methods known by those skilled in the art and then added or sprayed onto the animal feed.

Chemical modifications to the hop acids may, for example, increase the performance of the hops acids by increasing the efficacy, potency, stability, palatability, etc. For example, chemically modified derivatives of hop acids such as hexahydrocolupulone and tetrahydroisohumulone have demonstrated antibacterial properties, as disclosed in U.S. Pat. No. 5,455,038, which is incorporated herein by reference in its entirety. Such chemical modifications of the hop acids are within the skill of persons skilled in the art. The present invention thus also includes the use of such modified hop acids. Of course the salt forms of the hop acids and their derivatives, including, for example, sodium and potassium salts and any solvates thereof, and any hydrogenated derivatives of the hop acids, may also be used according to the invention.

When hop acids are added to the feed or water, the hop acids may be added as a mixture of alpha and beta acids. When a mixture of alpha and beta acids is used it is preferable that the beta acids are present in a higher concentration than the alpha acids. The beta acids have more potent antimicrobial effect and less bitter taste than the alpha acids, and thus tend to have less impact on palatability. Although they tend to impart more bitter flavor, the alpha acids may also be used with substantially no beta acids. If a mixture of beta and alpha acids is used, in one embodiment the beta acids are present at a 8:1 ratio to the alpha acids. In another embodiment, only beta acids are used. In hop varieties in current commercial production the ratio of alpha to beta varies from about 0.8 to about 3.6, with the exception of TEAMAKER, which has an alpha acid/beta acid ratio of about 0.1.

In accordance with the invention, the hop acids are supplemented to animals at a rate below that at which the acids decrease the palatability of the food and decrease food intake. Thus, the hop acids are administered in a palatable concentration. This concentration will of course vary with the type and palatability of the feed being supplemented, and the concentration of the hop acids may need to be adjusted accordingly. Such adjustments of the supplementation rate are within the skill of the person of ordinary skill in the art. Preferably, the hop acids may be administered to animals at a dosage of about 0.01-0.5 mg per pound animal weight per day. More preferably, the hop acids are administered at a dosage of about 0.02-0.2 mg per pound, and most preferably at a dosage of about 0.04-0.1 mg per pound.

To feedlot cattle, the hop acids can be administered at a dosage of about 2 mg to about 20 mg of hop acids per 100 pounds body weight, preferably at a dosage rate of about 4 mg to about 10 mg per 100 pounds. The hop acids may be administered orally, or in drinking water, or as a feed supplement. When added to the animal's feed at the rates given above, the form of the feed must be taken into account. For example, feedlot cattle are generally fed a mixture of grain, grass hay and alfalfa hay, and it is preferable for simplicity, although not essential, to add the hops or the hop acids to the grain portion of the feed. Alfalfa hay is frequently fed in pellet form, and the hops or hop acids can be incorporated into the alfalfa pellets. Dairy cattle are often fed a mixture of grain, alfalfa hay and silage, and the hops or hop acids are most conveniently added to the grain portion of the diet, generally at a dosage rate of between 25 and 150 mg of hop acids per animal per day. For poultry, which generally are self-feeders, an appropriate dose would be about 1 mg to about 25 mg of hop acids per pound of feed, although poultry may be able to ingest higher concentrations of the hop acids.

As antibiotics, providing hop acids to the digestive tract of animals (from ingestion of hop cones or hop acids) will alter the microbial population of the gastrointestinal tract by killing or inhibiting/reducing the growth of the microbes or by altering the microbial metabolism. In addition, the hop acids would be expected to kill or inhibit/reduce the growth of pathogenic organisms in the digestive tract of the animal. Exemplary pathogenic organisms include, but are not limited to, *Clostridium* species, including *Clostridium chauvoei* which causes blackleg, *Clostridium botulinum* which causes botulism, and *Clostridium tetani* which causes tetanus, *Clostridium perfringens* which causes necrotic enteritis, *Listeria* species which cause listeriosis, *Nocardia* species which cause nocardiosis, *Bacillus* species, including *Bacillus anthracis* which causes anthrax, *Mycobacterium tuberculosis*, which causes bovine tuberculosis, and various species of *Streptococcus*. Further organisms susceptible to the activity of hop acids include those responsible for causing mastitis in dairy cattle, sheep and goats, such as *Staphylococcus aureus, Streptococcus uberis, Streptococcus agalactiae*, and *Streptococcus dysgalactiae. Actinomyces pyogenes, Pseudomonas* and other infections, which are less prevalent, may also be prevented or reduced in incidence through the use of the present invention. As another example, protozoa, such as *Eimeria* species, e.g., *E. tenella, E. necatrix, E. acervulina* and *E. maxima*, would also be expected to be susceptible to the activity of hop acids.

Because of the antibiotic activity of the hop acids, when animals, such as dairy and beef cattle are fed the acids, they should show better health, vigor, weight gain and freedom from diseases. The administration of hop acids should also decrease the incidence of conditions such as mastitis and bovine tuberculosis in dairy cattle, and anthrax in beef cattle. These results are similar to the goals achieved by the traditional practice of adding antibiotics to animal feed.

In addition, beef cattle that have ingested hops or hop acids should have an altered digestive pattern. Cattle having been fed hops or hop acids should be able to ingest a much higher level of molasses before they begin to pass undigested grain. Livestock feeders like to include a high level of molasses in animal feed because it is a cheap source of carbohydrate. However, it has been observed that high amounts of molasses cause the cattle to pass undigested grain. The administration of hops or hop acids would be expected to ameliorate or alleviate this type of problem. Thus, the present invention would be expected to enhance weight gain in animals.

When animals ingest hops or hop acids, they should demonstrate a faster rate of weight gain when compared to animals not ingesting the hops or hop acids. Without being bound by theory, it is believed that the administration of hop acids will cause the animals to remain healthier relative to animals not being supplemented, thereby allowing them to ingest more food and thus gain weight easier and quicker. Also, it is believed that the presence of antibiotics, here the hop acids, in the gastrointestinal tract of animals alters the microbial population and inhibits the growth of undesirable pathogenic organisms in the tract. Thus, the food nutrients ingested by the animal are more efficiently directed to growth of the animal. The present invention, therefore, also provides a method for increasing weight gain in animals. This method comprises feeding hops or hop acids to the animals. When the animal ingests the hops or hop acids, the presence of hop acids in the animal's digestive tract provides for an increase in weight gain over the weight gain in animals not ingesting the hops or hop acids. The animals are preferably beef cattle, dairy cattle, sheep, swine, horses or poultry. The hops or hop acids are as described above.

Because animals ingesting antibiotics, e.g., hops or hop acids, stay healthier, and because of putative alterations in the makeup of the gastrointestinal flora, there is an increase in the efficiency with which animals convert food to meat, milk and eggs. Thus, the present invention also provides a method for increasing feed efficiency in animals. This method comprises feeding palatable concentrations of hops or hop acids to the animals. When the animal ingests the hops or hop acids, the presence of hop acids in the animal's digestive tract provides an increase in feed efficiency over feed efficiency in animals not ingesting the hops or hop acids. The animals are preferably beef cattle, dairy cattle, sheep, swine, horses or poultry. The hops or hop acids are as described above.

When dairy animals are fed hops or hop acids, they exhibit an increase in milk production. Not being bound by theory, since the hop acids decrease the risk of mastitis and other illness and positively influence feed utilization, the nutrients and calories present in the animal feed are more efficiently directed to growth of the animal and milk production. The decreased incidence of mastitis alone would provide for an increase in milk production since mastitis often stops milk production or at the very least renders the milk unfit for consumption, potentially leading to its disposal. Thus, the present invention also provides a method for increasing milk production in dairy animals. The invention comprises methods comprising feeding palatable concentrations of hops or hop acids to the dairy animals, and it further comprises feeds containing palatable concentrations of hop acids. Preferred dairy animals include cattle, goats, or sheep. The hops or hop acids are as described above.

Poultry ingesting hops or hop acids in their feed would be expected to remain healthier and in turn show an increase in egg and meat production over poultry not ingesting hops or hop acids. Not being bound by theory, because of the decreased incidence of infection and increase in feed efficiency, the nutrients and calories provided in the poultry feed may be more efficiently directed to growth of the animal and egg production. Thus, the present invention provides a method for increasing egg production in poultry. The method of the present invention comprises feeding hops and/or hop acids to the poultry in palatable concentrations and feeds containing palatable concentrations of hops or hop acids for feeding to poultry. The presence of hop acids in the bird's digestive tract provides for an increase in egg production over the egg production in poultry not ingesting the hop cones or hop acids. The hops or hop acids are as described above. In addition, hop acids are effective against *Listeria* organisms, which can be a significant cause of contamination in poultry production. By inhibiting the growth of *Listeria* sp. in the digestive tracts of poultry, the present invention would help to decrease or prevent the contamination of poultry carcasses during processing.

The present invention also provides animal feeds containing palatable concentrations of hops or hop acids. The composition of feeds for the farm animals discussed herein are well known in the art and such feeds are widely available commercially. Hop acids may be mixed into the feed in any of a number of ways that will be apparent to those of skill in the art, e.g., the hop acids may be added as dried and milled hops or as solutions of hop acids. As used herein the terms "mill," "milling," "milled," or the like, refers to processes for grinding, crushing, crumbling, compressing, rolling, or otherwise reducing the size of the hop plant (e.g., cone) particles or pieces. Such milling can, for example, reduce hop cones to a powder or small granules.

Hop producers in the U.S., U.K. and Germany produce very large quantities of solutions of hop acids, usually in the form of potassium salts in water. The most common solutions contain about 10% beta acids and about 30% isoalpha acids. Beta acids are available commercially available from Haas (Betastab 10A), usually as a 10% solution of a potassium salt at pH 12 to pH 13. Commercial isoalpha acid solutions are available that contain approximately 30% isoalpha acids as the potassium salts in water at pH 8 to pH 9. Alpha acid solutions are an intermediate product in the manufacture of isoalpha acids and are available on demand from commercial manufacturers of hop acids. Solutions of the hydrogenated forms of the isoalpha acids are commercially available, usually as 10% solutions in water as the potassium salts, and hydrogenated forms of the beta acids are also available on demand. The isomerized hop acids are available from Kalsec (ISOLONE®), Haas (Isomerized hop extract), and Steiner (Isoextract 30%). Dihydro isomerized acids are available from Kalsec (HYDROLONE®). Tetrahydro isomerized acids are available from Kalsec (TETRALONE®), Haas (TETRAHOP GOLD®), and Steiner (Tetra-Isoextract 10%). Hexahydro isomerized acids are available from Kalsec (HEXALONE®), and Haas (HEXAHOP GOLD). Thus, products for use as a feed additive can be formulated that contain hop acid solutions in any desired concentration. Preferably, the hop acids are utilized at concentrations below about 10% as the potassium salts in alkaline water. These solutions of hop acids can be mixed into or sprayed onto the feed at the desired rate to create a feed having the desired concentration of hop acids. Alternatively, the hop acids may be mixed with molasses and mixed into the animals' feed, which is common practice in the cattle feeding industry.

With regard to milled hops, hop cones are initially milled and pelletized. The alpha acids may be present either in the natural state or isomerised. The pellets are either vacuum packed or packed under an inert atmosphere. The concentration of hop acids in milled hops depends on the content in the hop cone which is dependent on growing season and hop variety. Hop varieties are available with alpha acid contents ranging from about 4% up to about 18% and beta acid contents ranging from about 2% up to about 10% in the dried cones. Preferably, the hops are milled and pelletized and isomerized if required. The isomerized and unisomerized pellets are then blended in the desired ratio and then milled again to form a blended powder. Milling, pelletizing and then milling a second time increases the bulk density from about 8 lbs per cubic foot to about 27 lbs per cubic foot, which provides savings in packaging, storage and shipping compared to unpelletized hops. The milled hops can then be blended with the animal feed according to methods known to those skilled in the art.

In one embodiment, the invention provides animal feeds containing about 25 mg to about 1000 mg of hop acids per 100 pounds of feed. In a preferred embodiment, the feed would contain about 75 mg to about 400 mg per 100 pounds of feed. In a more preferred embodiment, the feed would contain about 100 to about 250 mg per 100 pounds of feed. In another embodiment, the invention provides animal feeds containing palatable concentrations of milled hops. Preferably, the concentration of milled hops in the feed would be about 0.4 grams to about 2.5 grams of milled hops per 100 pounds of feed. Most preferably the feed would contain about 0.5 grams to about 1.3 grams of milled hops per 100 pounds of feed.

There are several feed companies that supply feeds specifically formulated for the type of animal being fed. The hop acids described herein, as exemplified by Examples 1 and 2 below, can be added to these commercial formulations. Alternatively, farmers, ranchers or feedlot operators can prepare feeds suitable for their production animals. For cattle and other livestock, suitable feeds are generally mixtures of well-known cereal grains or forage crops, and may have added vitamin and/or mineral supplements. Appropriate guides for the addition of antibiotic supplements can be found in veterinary texts, for example Ensminger, M. E., *Animal Science* (9th ed.), Interstate Publishers Inc., Danville Ill.

It will be understood that the hop acid additive should be mixed into the feed in the most practical way, and if the animal's diet is partly mixed grains and partly fodder, such as hay, the milled hops should generally be added to the mixed grain portion (although the liquid hop acids could be sprayed onto any portion of the animal's feed). It should be further understood that hops are a natural crop and they will vary in content of hop acids from crop to crop and batch to batch. Analyses for the acids are routinely performed in the hop industry and the amount of milled hops used in the animal feed must be adjusted according to the analyses.

EXAMPLE 1

Dry Product

Commercial isomerised and non-isomerised hop pellets, as used by brewers, are mixed together in equal amounts. The non-isomerised pellets contain 12.6% alpha acids and 7.6% beta acids. The isomerised pellets contain 0.3% alpha acids, 10.5% isoalpha acids and 6.5% beta acids. The mixed pellets are ground in a hammermill to form a powder. The powder contains 6.2% alpha acids, 5.2% isoalpha acids and 7.1% beta acids. This milled hop powder is then blended with animal feeds according to methods known in the art to create feeds having the desired concentrations of hop acids according to the invention. The powder should be mixed into the feed within two weeks after milling the pellets.

EXAMPLE 2

Liquid Product

A typical product could be a mixture prepared by combining one part of alpha acid solutions, 30% alpha acids, with one part of isoalpha solution, 30% isoalpha acids, and three parts of beta acid solution, 10% beta acids. The resulting solution contains 6% of each of the hop acids. This solution is diluted by adding 19 parts water to one part of the hop acid solution and sprayed onto the animal feed at a rate of 16 ml of hop acid solution per 100 lbs of animal feed, to create a feed containing 1.44 mg of hop acids per pound of animal feed. The solution of mixed acids should be mixed (by, for example, stirring, shaking, agitating etc.) during the addition to the feed.

EXAMPLE 3

Feedlot Cattle Formulation

Addition of dry antibiotic from Example 1 is added to a feed formulation suitable for feedlot beef cattle weighing from about 200 to about 800 pounds. Suitable feed formulations would be well understood to those of skill in this field. In one embodiment, feeds are prepared containing about 50 to about 400 mg of hop acids per 100 pounds of feed. These amounts of hop acids will be present in feed having added to it about 270 mg to about 2160 mg of milled hops produced according to Example 1, per 100 pounds of feed. In another embodiment, about 400 mg to about 1000 mg of the milled hops produced according to Example 1 are added per 100 pounds of feed. A 700 pound animal consuming 35 pounds of feed daily would ingest 25 to 65 mg of the hops acids daily eating this feed.

Thus, the production of animal feeds containing palatable concentrations of hop acids is disclosed, as are methods of administering hop acids to increase the feed efficiency, weight gain and milk, meat and egg production of mammals and poultry. Although preferred embodiments of the subject invention have been described in some detail, it is understood that obvious variations can be made without departing from the spirit and the scope of the invention.

We claim:

1. A supplemented animal feed comprising:
a prepared or formulated edible animal feed to which has been added a palatable and effective amount of milled hop cones having a beta acid content between about 2% up to about 10%,
wherein the palatable and effective amount of the milled hop cones comprises hop acids in an amount effective to enhance feed utilization in an animal.

2. The supplemented animal feed of claim 1, wherein the concentration of the milled hop cones is no more than about 2.5 grams of the milled hop cones per 100 pounds of feed.

3. The supplemented animal feed of claim 2, wherein the concentration of the milled hop cones is no less than about 0.4 grams of the milled hop cones per 100 pounds of feed.

4. The supplemented animal feed of claim 1, wherein the feed comprises mixed grains.

5. The supplemented animal feed of claim 1, wherein the milled hop cones have been pelletized.

6. The supplemented animal feed of claim 1, wherein the milled hop cones have been powderized.

7. A method of altering the microbial population of the gastrointestinal tract of a livestock animal in need thereof comprising administering to the livestock animal an effective amount of the supplemental animal feed according to claim 1.

8. The method of claim 7, wherein the ratio of $\beta$-hop acids to $\alpha$-hop acids in the milled hop cones is greater than about 1.

9. The method of claim 8, wherein the milled hop cones are made from TEAMAKER hops.

10. The method of claim 7, wherein the concentration of the milled hop cones provided to the animal is no more than about 2.5 grams of the milled hop cones per 100 pounds of animal feed.

11. The method of claim 10, wherein the concentration of the milled hop cones is no less than about 0.4 grams of the milled hop cones per 100 pounds of livestock animal feed.

12. The method of claim 11, wherein the feed comprises mixed grains.

13. The method of claim 7, wherein the milled hop cones have been pelletized.

14. The method of claim 7, wherein the milled hop cones have been powderized.

15. The method of claim 7, wherein the livestock animal is a ruminant.

16. The method of claim 7, wherein the livestock animal is a breed of poultry.

17. The method of claim 7, wherein the livestock animal is a breed of swine.

* * * * *